United States Patent
Nguyen et al.

[19]

[11] Patent Number: 5,941,857
[45] Date of Patent: Aug. 24, 1999

[54] DISPOSABLE PEN NEEDLE

[75] Inventors: Tuan V. Nguyen, Rockaway; Michael A. Dibiasi, West Milford, both of N.J.

[73] Assignee: Becton Dickinson and Company, Franklin Lakes, N.J.

[21] Appl. No.: 08/928,876

[22] Filed: Sep. 12, 1997

[51] Int. Cl.[6] .................................................. A61M 5/00
[52] U.S. Cl. ....................... 604/263; 604/195; 604/198
[58] Field of Search .................................. 604/192, 195, 604/198, 110, 263; 206/263–270, 438

[56] References Cited

U.S. PATENT DOCUMENTS 5,342,323  8/1994  Haining ................................. 604/195

*Primary Examiner*—Wynn Wood Coggins
*Assistant Examiner*—Deborah Blyveis
*Attorney, Agent, or Firm*—Alan W. Fiedler

[57] ABSTRACT

A disposable pen needle assembly is provided that includes a snap lock feature that provides a user with a simple method of detaching and attaching the pen needle to the medication delivery pen. In addition, the pen needle assembly includes a multi-use shield that initially shields the distal end of the pen needle prior to use and then both shields the proximal end of the needle and locks the used needle in its outer cover prior to disposal.

8 Claims, 5 Drawing Sheets

DISPOSABLE PEN NEEDLE

BACKGROUND OF THE INVENTION

1. Field of the Invention

The subject invention relates to a safe disposable pen needle for use on a medication delivery pen having a cartridge assembly and a pen body assembly.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula is mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication is drawn into the chamber of the syringe barrel by moving the plunger a selected distance in a proximal direction. The needle cannula is withdrawn from the vial, and the medication is injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a cartridge holder into which a cartridge of insulin or other medication may be received. The cartridge holder is an elongate generally tubular structure with proximal and distal ends. The distal end of the prior art cartridge holder includes mounting means for engaging a double-ended needle cannula. The proximal end also includes mounting means for engaging a driver and dose setting apparatus as explained further below. A disposable cartridge for use with the prior art cartridge holder includes a distal end having a pierceable elastomeric seal that can be pierced by one end of a double-ended needle cannula. The proximal end of this prior art cartridge includes a plunger slidably disposed in fluid tight engagement with the cylindrical wall of the cartridge. This prior art medication delivery pen is used by inserting the cartridge of medication into the cartridge holder. A prior art pen body then is connected to the proximal end of the cartridge holder. The pen body includes a dose setting apparatus for designating a dose of medication to be delivered by the pen and a driving apparatus for urging the plunger of the cartridge distally for a distance corresponding to the selected dose.

The user of the pen mounts a prior art double-ended needle cannula to the distal end of the cartridge holder such that the proximal point of the needle cannula pierces the elastomeric seal on the cartridge. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the cartridge will become exhausted after several such administrations of medication. The patient then separates the cartridge holder from the pen body. The empty cartridge may then be removed and discarded. A new cartridge can be inserted into the cartridge holder, and the cartridge holder and pen body can be reassembled and used as explained above.

The above described medication delivery pen is effective and much more convenient for self-administration of medication than the typical hypodermic syringe and separate medication vial. However, after using the prior art double-ended pen needle the user was required to take care in disposing of the pen needle to prevent an accidental needle stick. For example, the prior art double-ended pen needle would be provided to the user with an shield covering the distal end of the pen needle and contained and sealed within an outer cover by a label or sterility barrier. The user would then remove the sterility barrier, use the outer cover to mount the double-ended pen needle to the distal end of the medication delivery pen, remove the outer cover, and perform the injection. Then, the user would use the outer cover to remove the double-ended pen needle from the medication delivery pen and then dispose of the outer cover containing the used double-ended pen needle in a sharps collector.

Since the proximal end of the double-ended needle is not covered prior to placing the used double-ended needle into the sharps collector, there remains a risk of an accidental needle stick occurring if someone touches the proximal point of the double-ended needle inside the outer covering. In addition, there is also the risk that a user would attempt to reshield the needle with the shield rather than simply dispose of the shield, which also raises a risk of an accidental needle stick occurring during such a reshielding process.

SUMMARY OF THE INVENTION

The subject invention relates to a disposable pen needle assembly for a medication delivery pen that overcomes the problems associated with the prior art double-ended pen needle by providing a pen needle that is easy to dispose of safely.

The disposable pen needle assembly of the present invention prevents an unused shielded pen needle assembly from moving into a locked position within an outer cover, but permits a used unshielded pen needle assembly to snap lock into a locked position within the outer cover. This feature is provided by the specially designed multi-use shield that is used initially to shield the distal end of the pen needle prior to use and is then used to both shield the proximal end of the pen needle and lock the used pen needle in the outer cover after use prior to safe disposal.

An object of the present invention is to prevent the pen needle from being reused by having it locked and covered in the outer cover. In addition, the present invention provides a user with a convenient way to carry and dispose of their personal pen needles.

These and other aspects, features and advantages of the present invention will become apparent from the following detailed description taken in conjunction with the accompanying drawings.

DETAILED DESCRIPTION

Figure 1:
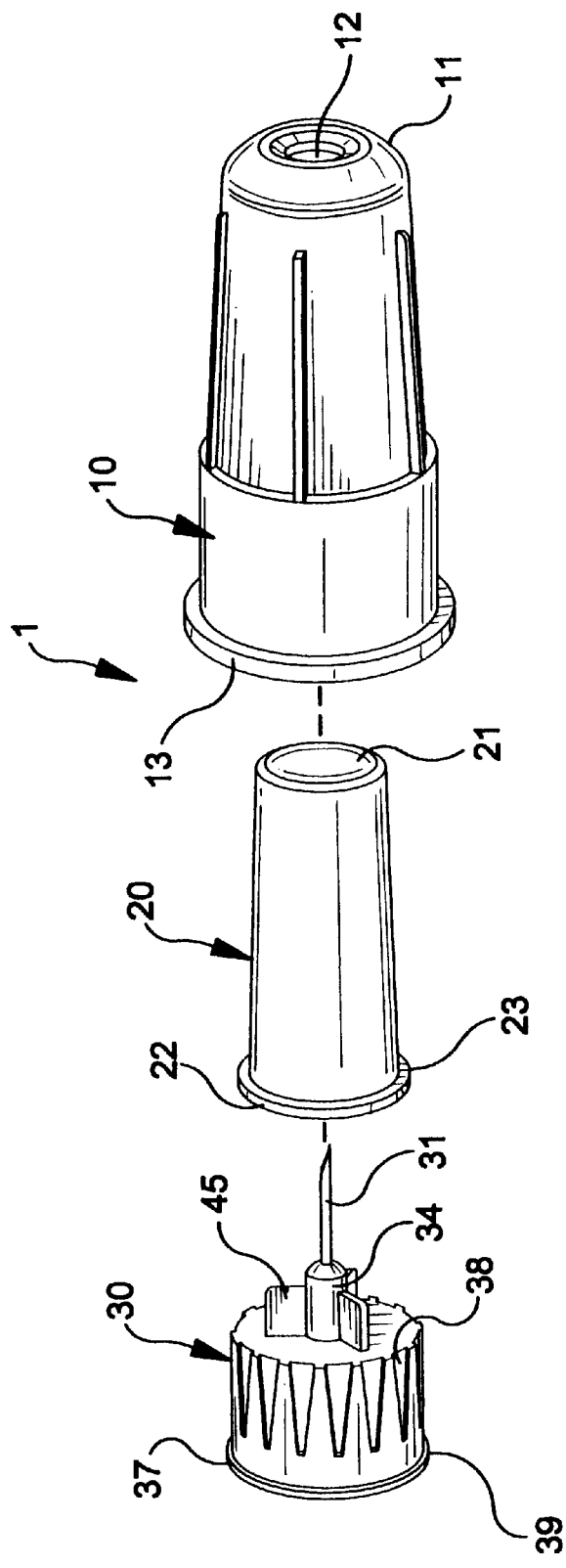
FIG. 1 is an exploded perspective view of a pen needle assembly according to the present invention.
Figure 2:
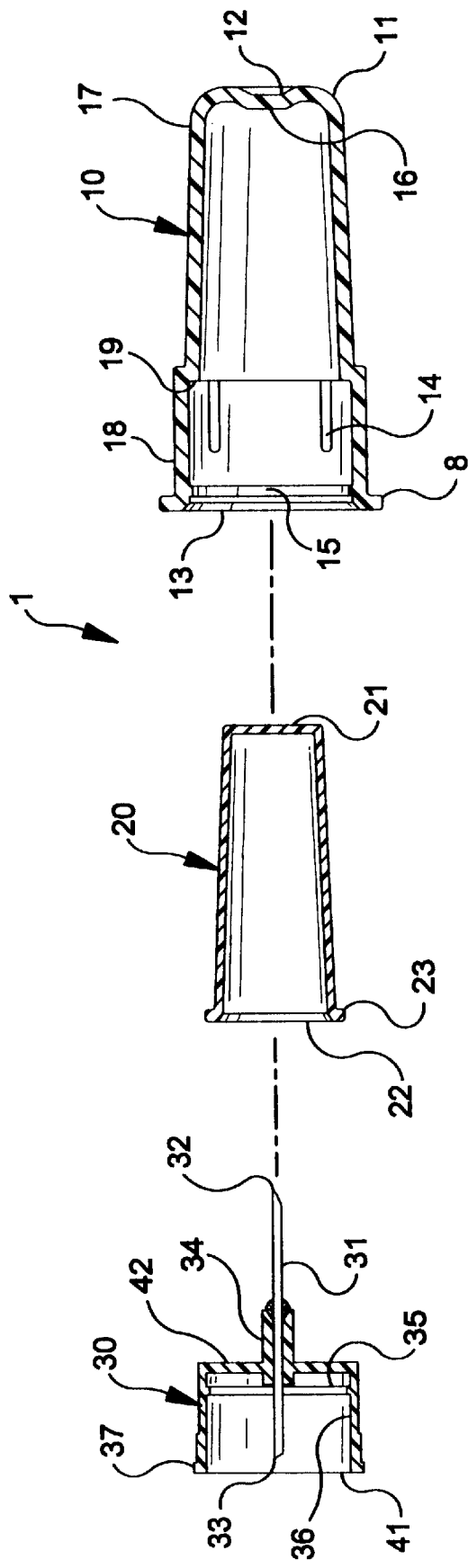
FIG. 2 is an exploded cross-sectional view of the pen needle assembly shown in FIG. 1.
Figure 3:
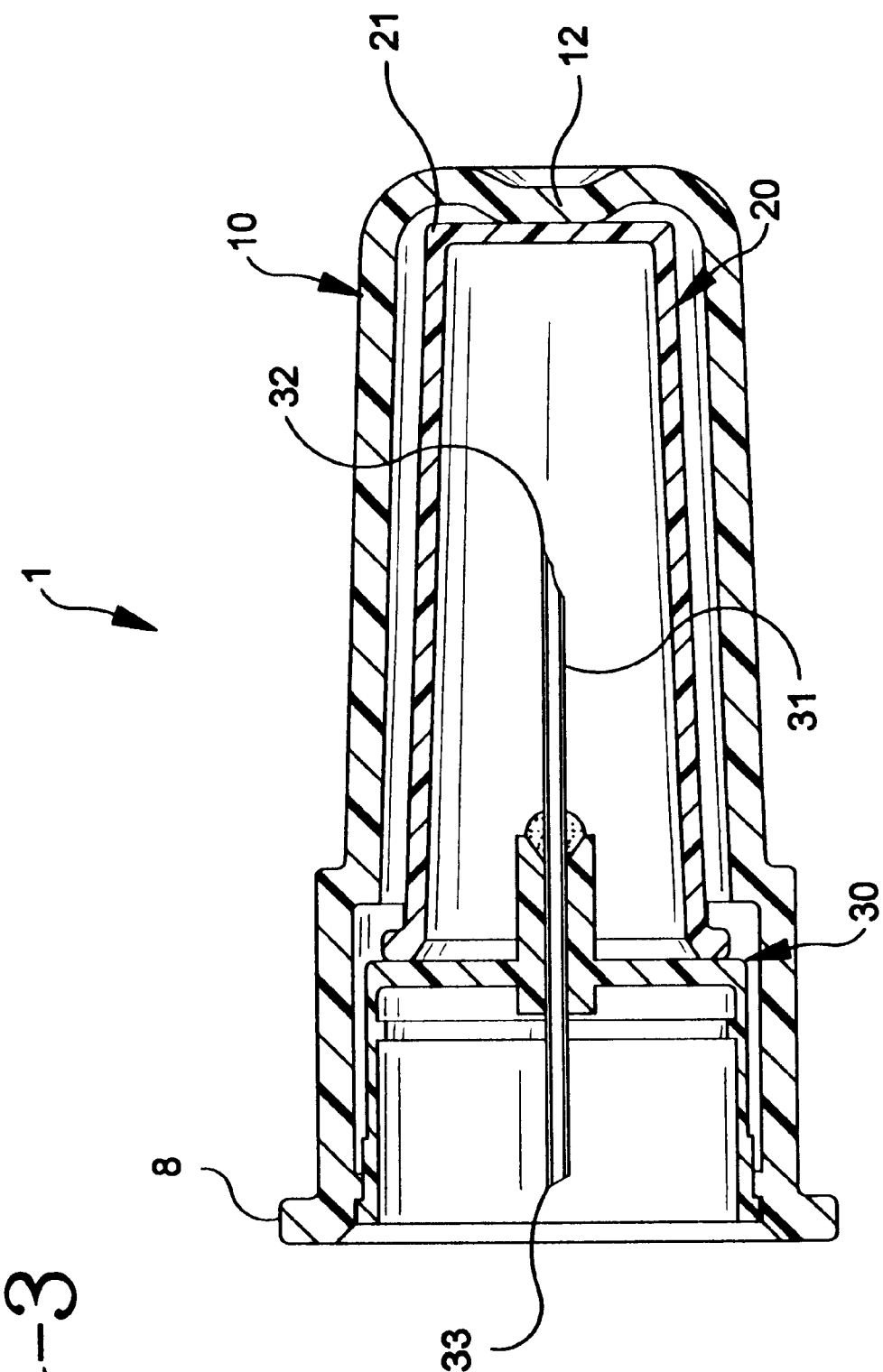
FIG. 3 is a cross-sectional view of the pen needle assembly shown in FIG. 1 as original assembled for delivery.

A disposable pen needle assembly in accordance with the subject invention is identified generally by the numeral 1 in FIG. 1. FIG. 1 shows an exploded perspective view of pen needle assembly 1 and its three major components including an outer cover 10, a shield 20 and a pen needle 30. FIG. 2 shows an exploded cross-sectional view of pen needle assembly 1 with each of its major components and FIG. 3 shows a cross-sectional view of pen needle assembly 1 as originally assembled for delivery.

Outer cover 10 includes a distal end 11 having a central recess 12 that forms an inner surface 16 at distal end 11 extending into outer cover 10 in a proximal direction. Outer cover 10 also includes a retaining ring 15 within an open proximal end 13 and a number of laterally extending splines 14. Outer cover 10 is divided into two sections including a narrow section 17 towards distal end 11 and an expanded section 18 towards proximal end 13. A shelf 19 is provided within outer cover 10 where expanded section 18 meets narrow section 17. Outer cover 10 also includes a flange 8 extending from proximal end 13 to which a label or sterility barrier (not shown) is attached after pen needle 30 and shield 20 have been assembled into outer cover 10, as shown in FIG. 3.

Shield 20 includes a closed distal end 21 and an open proximal end 22 having a locking flange 23 extending from open proximal end 22.

Pen needle 30 includes a skirt 39 having an open proximal end 41 and a distal end 42 having a hub 34 extending therefrom. A needle cannula 31 is mounted within hub 34 and includes a distal point 32 and a proximal point 33, wherein proximal point 33 is within skirt 39 and distal point 32 extends out of hub 34. Skirt 39 includes an inner surface 36 having a locking ring 35 extending therefrom. In addition, skirt 39 also includes a retaining flange 37 extending from open proximal end 41. Pen needle 30 also includes a plurality of tabs 45 extending from hub 34 dimensioned to be received within open proximal end 22 of shield 20 when pen needle assembly 1 is originally assembled for delivery as shown in FIG. 3.

After shield 20 has been mounted on pen needle 30 the assembled unit is inserted into open proximal end 13 of outer cover 10 until distal end 21 of shield 20 is stopped by contacting inner surface 16 of recess 12 at distal end 11 of outer cover 10. As shown in FIG. 3, in this arrangement, pen needle 30 with attached shield 20 is slideably received within outer cover 10 and can be easily removed since it is not locked or permanently retained therein except by a label or sterility barrier (not shown) that may be attached over flange 8. In this arrangement, splines 14 on the inner surface of outer cover 10 engage with the outer channels 38 on the outside of skirt 39 of pen needle 30. This arrangement would prevent pen needle 30 from rotating within outer cover 10 if skirt 39 of pen needle 30 is of the type having threads for mating with the distal end of a medication delivery pen. Of course, if skirt 39 of pen needle 30 is of the type having a snap ring 35, like that shown in FIGS. 2, 3 and 5, preventing rotation of pen needle 30 is not required.

Attachment of pen needle 30 to the distal end of a medication delivery pen would be performed using a standard push-pull movement. Snap ring 35 is designed to snap on to the distal end of the medication delivery pen when the distal end of the medication delivery pen is inserted into open proximal end 41 of skirt 39 and pushed therein until snap ring 35 engages a corresponding ring on the distal end of the medication delivery pen. After pen needle 30 has been mounted on the medication delivery pen, shield 20 is removed from pen needle 30 to uncover distal point 32 so that the injection may be performed. In the present invention, shield 20 must be retained by the user to perform the operation described below. Presently, users are advised to dispose of the inner shield provided on the pen needles currently available.

According to the present invention, after the injection has been made by the user the unshielded pen needle 30 on the medication delivery pen is inserted into open proximal end 13 of outer cover 10 until distal end 42 of pen needle 30 comes into contact with shelf 19 within outer cover 10 and retaining flange 37 at open proximal end 41 of skirt 39 has engaged retaining ring 15 within open proximal end 13 of outer cover 10. When this has occurred, the medication delivery pen can be pulled and unsnapped from skirt 39 of pen needle 30.

Figure 4:
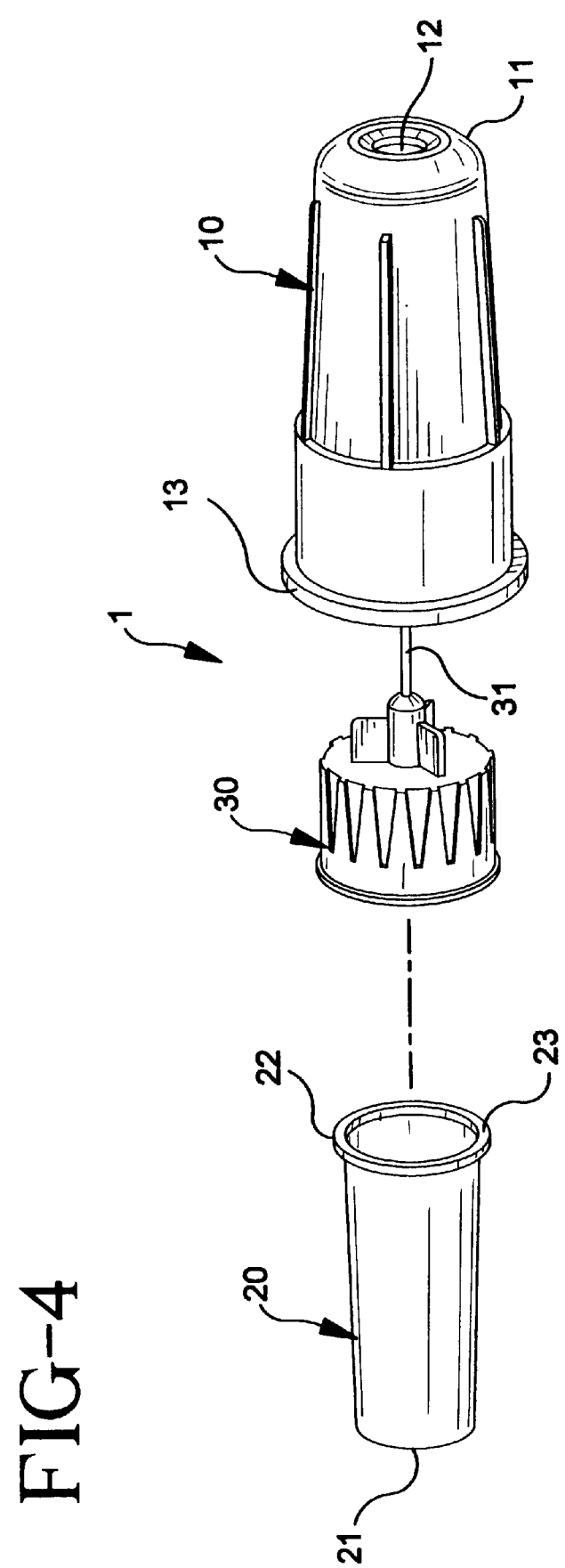
FIG. 4 is an exploded perspective view of the pen needle assembly shown in FIG. 1 after being used.
Figure 5:
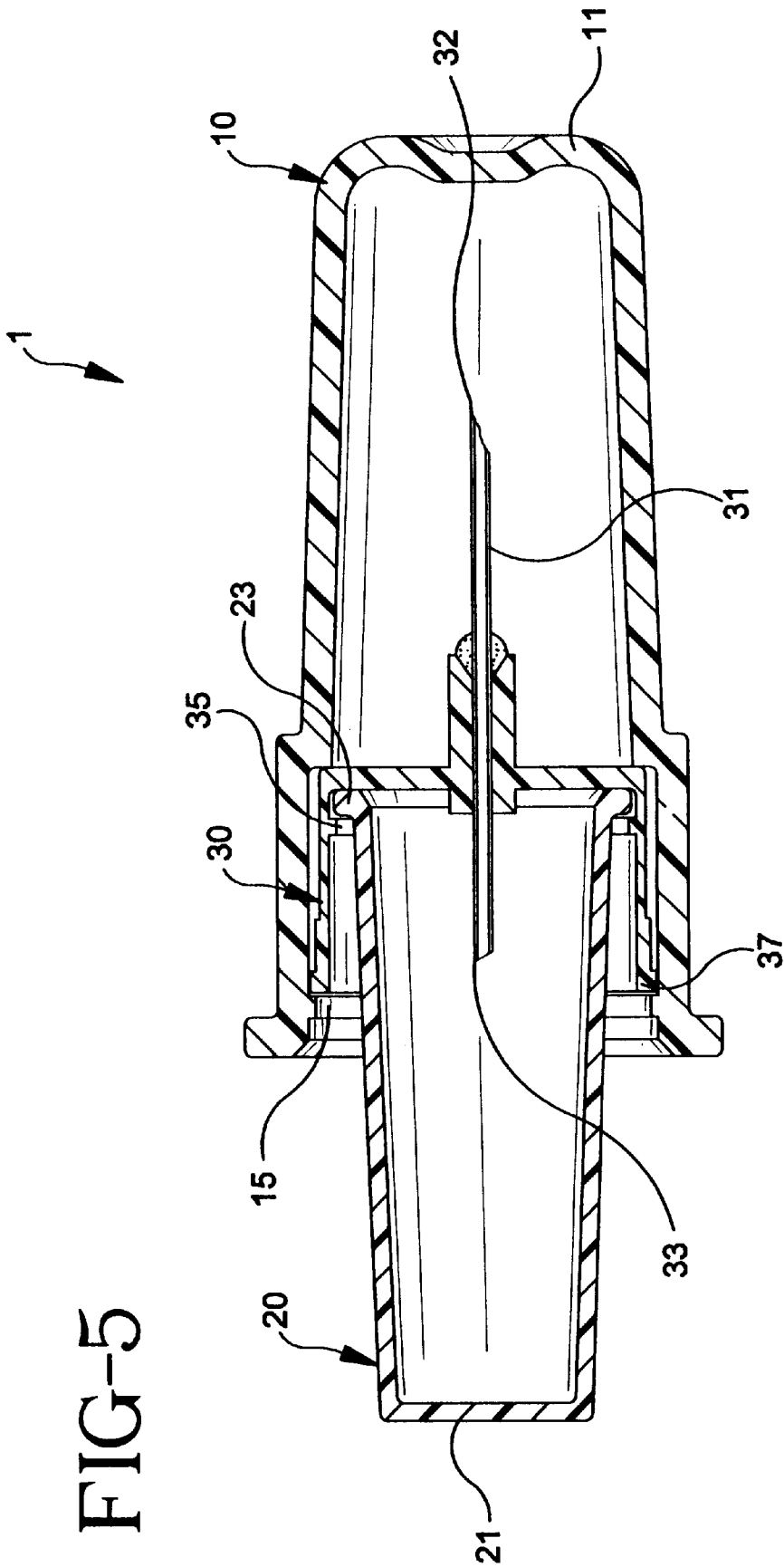
FIG. 5 is a cross-sectional view of the pen needle assembly shown in FIG. 4 assembled for disposal.

Then, as shown in FIGS. 4 and 5, open proximal end 22 of shield 20 is pushed into open proximal end 13 of outer cover 10 until locking flange 23 on shield 20 engages locking ring 35 within skirt 39 on pen needle 30. When shield 20 has been assembled with outer cover 10, as shown in FIG. 5, shield 20 cannot be removed from outer cover 10 so that pen needle 30 is permanently encapsulated within shield 20 and outer cover 10. This new design removes any risk of accidental needle sticks since distal point 32 and proximal point 33 of pen needle 30 are surrounded by outer cover 10 and shield 20, respectively.

While the invention has been described with respect to a preferred embodiment, it is apparent that various changes can be made without departing from the scope of the invention as defined by the appended claims.

What is claimed is:

1. A pen needle assembly comprising:
    a pen needle having a skirt and a cannula including a distal point and a proximal point;
    a cover having an open proximal end and a closed distal end for receiving said pen needle;
    a shield having a closed distal end and an open proximal end for mounting on said pen needle to shield said distal point of said pen needle;
    means for preventing said pen needle from moving from an unlocked position to a locked position within said cover prior to use;

means for locking said pen needle in the locked position within said cover after use; and means for preventing said pen needle from rotating within said cover.

2. A pen needle assembly according to claim 1, wherein said means for preventing said pen needle from moving from the unlocked position to the locked position within said cover includes a recess at said closed distal end of said cover that contacts said closed distal end of said shield when said shield is mounted over said distal point of said pen needle and said shielded pen needle is inserted into said open proximal end of said cover.

3. A pen needle assembly according to claim 1, wherein said means for locking said pen needle in the locked position within said cover includes:

a retaining flange on said skirt of said pen needle; and a retaining ring within said open proximal end of said cover, said retaining ring engaging said retaining flange on said pen needle to lock said pen needle in the locked position, when said unshielded pen needle is inserted into said open proximal end of said cover.

4. A pen needle assembly according to claim 3, further comprising means for permanently locking said open proximal end of said shield to said open proximal end of said pen needle when said pen needle is in the locked position within said cover.

5. A pen needle assembly according to claim 4, wherein said means for permanently locking said open proximal end of said shield to said open proximal end of said pen needle includes:

a locking ring within said skirt of said pen needle; and a locking flange on said open proximal end of said shield that engages said locking ring within said pen needle when said open proximal end of said shield is inserted into said open proximal end of said skirt on said pen needle.

6. A pen needle assembly according to claim 1, further comprising means for permanently locking said open proximal end of said shield to said open proximal end of said pen needle when said pen needle is in the locked position within said cover.

7. A pen needle assembly according to claim 6, wherein said means for permanently locking said open proximal end of said shield to said open proximal end of said pen needle includes:

a locking ring within said skirt of said pen needle; and a locking flange on said open proximal end of said shield that engages said locking ring within said pen needle when said open proximal end of said shield is to said open proximal end of said skirt on said pen needle.

8. A pen needle assembly according to claim 1, wherein said means for preventing said pen needle from rotating within said cover includes:

a plurality of splines on said inner surface of said cover; and a plurality of outer channels on said skirt of said pen needle that engage with said plurality of splines within said cover.

* * * * *